United States Patent
Kalra et al.

(10) Patent No.: US 10,647,932 B2
(45) Date of Patent: May 12, 2020

(54) PROCESSES AND APPARATUSES FOR OLEFIN SATURATION IN AN AROMATICS COMPLEX

(71) Applicant: UOP LLC, Des Plaines, IL (US)

(72) Inventors: Jalesh Kalra, Naperville, IL (US); Robert J. L. Noe, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/987,871

(22) Filed: May 23, 2018

(65) Prior Publication Data

US 2018/0265791 A1    Sep. 20, 2018

Related U.S. Application Data

(63) Continuation of application No. PCT/US2016/063069, filed on Nov. 21, 2016.
(Continued)

(51) Int. Cl.
*C10G 67/14*      (2006.01)
*C07C 6/12*       (2006.01)
(Continued)

(52) U.S. Cl.
CPC .............. *C10G 67/14* (2013.01); *C07C 5/03* (2013.01); *C07C 5/2729* (2013.01); *C07C 6/126* (2013.01);
(Continued)

(58) Field of Classification Search
CPC .... C10G 67/14; C10G 53/04; C10G 67/0418; C10G 67/02; C10G 67/0427;
(Continued)

(56) References Cited

U.S. PATENT DOCUMENTS

| 2,840,620 A | 6/1958 | Gerhold et al. |
| 5,952,536 A * | 9/1999 | Nacamuli ................. C07C 6/12 585/474 |

(Continued)

FOREIGN PATENT DOCUMENTS

| KR | 20100014309 A | 2/2010 |
| KR | 20110051473 A | 5/2011 |

(Continued)

OTHER PUBLICATIONS

International Search Report from corresponding PCT application No. PCT/US2016/063069, dated Mar. 16, 2017.
(Continued)

*Primary Examiner* — Ali Z Fadhel

(57) ABSTRACT

Process and apparatuses for producing benzene and paraxylene from a reformate stream is provided. The process comprises separating the reformate stream to provide a first stream comprising $C_4$ and lighter hydrocarbons and a second stream comprising aromatic hydrocarbons. The second steam is provided to a reformate splitter to provide a reformate bottoms stream comprising $C_{8+}$ aromatic hydrocarbons and a reformate overhead stream comprising $C_{7-}$ aromatic hydrocarbons. The reformate overhead stream is passed to an aromatics extraction unit to provide an aromatics extract stream comprising benzene and toluene and a raffinate stream comprising non-aromatic hydrocarbons. The reformate bottoms stream and one of the first stream and the raffinate stream is passed to an olefin reduction zone, wherein the reformate bottoms stream and one of the first stream and the raffinate stream are contacted with an olefin saturation catalyst under olefin saturation conditions to produce an olefin-treated reformate stream.

18 Claims, 2 Drawing Sheets

Related U.S. Application Data

(60) Provisional application No. 62/268,022, filed on Dec. 16, 2015.

(51) Int. Cl.
| | |
|---|---|
| *C07C 7/04* | (2006.01) |
| *C07C 7/09* | (2006.01) |
| *C07C 7/08* | (2006.01) |
| *C10G 67/04* | (2006.01) |
| *C10G 53/04* | (2006.01) |
| *C07C 5/03* | (2006.01) |
| *C07C 5/27* | (2006.01) |
| *C07C 7/10* | (2006.01) |
| *C10G 53/02* | (2006.01) |
| *C10G 53/00* | (2006.01) |
| *C10G 67/00* | (2006.01) |
| *C10G 67/02* | (2006.01) |

(52) U.S. Cl.
CPC ............... *C07C 7/04* (2013.01); *C07C 7/08* (2013.01); *C07C 7/09* (2013.01); *C07C 7/10* (2013.01); *C10G 53/04* (2013.01); *C10G 67/0418* (2013.01); *C10G 53/00* (2013.01); *C10G 53/02* (2013.01); *C10G 67/00* (2013.01); *C10G 67/02* (2013.01); *C10G 67/0409* (2013.01); *C10G 67/0427* (2013.01); *C10G 2400/30* (2013.01)

(58) Field of Classification Search
CPC .... C10G 67/0409; C10G 67/00; C10G 53/00; C10G 53/02; C10G 2400/30; C07C 5/03; C07C 7/08; C07C 7/09; C07C 7/10; C07C 5/2729; C07C 7/04; C07C 6/126; C07C 15/08; C07C 15/04
See application file for complete search history.

(56) References Cited

U.S. PATENT DOCUMENTS

| | | | |
|---|---|---|---|
| 6,004,452 A | 12/1999 | Ash et al. | |
| 6,740,788 B1* | 5/2004 | Maher | C10G 69/08 |
| | | | 585/319 |
| 7,687,674 B2 | 3/2010 | Wegerer | |
| 10,308,567 B2 | 6/2019 | Jin et al. | |
| 2008/0262278 A1 | 10/2008 | Casey et al. | |
| 2013/0158312 A1 | 6/2013 | Serban et al. | |
| 2014/0142364 A1* | 5/2014 | Io | B01D 3/14 |
| | | | 585/805 |
| 2015/0368571 A1* | 12/2015 | Mehlberg | C10G 69/08 |
| | | | 208/62 |

FOREIGN PATENT DOCUMENTS

| | | |
|---|---|---|
| KR | 20150066586 A | 6/2015 |
| WO | 2012170336 A2 | 12/2012 |

OTHER PUBLICATIONS

Written Opinion from corresponding PCT application No. PCT/US2016/063069, dated Feb. 10, 2017.
International Preliminary Report on Patentability from corresponding PCT application No. PCT/US2016/063069, dated Jun. 19, 2018.
Extended European Search Report for corresponding European application No. 16876339.9, dated Jul. 22, 2019.

* cited by examiner

PROCESSES AND APPARATUSES FOR OLEFIN SATURATION IN AN AROMATICS COMPLEX

CROSS-REFERENCE TO RELATED APPLICATIONS

This application is a Continuation of copending International Application No. PCT/US2016/063069 filed Nov. 21, 2016, which application claims priority from U.S. Provisional Application No. 62/268,022 filed Dec. 16, 2015, the contents of which cited applications are hereby incorporated by reference in their entirety.

TECHNICAL FIELD

The technical field generally relates to apparatuses and processes for producing benzene and para-xylene in an aromatics complex. More particularly, the technical field relates to apparatuses and processes for producing benzene and para-xylene from a reformate stream in an aromatics complex using a integrated scheme for saturation of olefins.

BACKGROUND

Most new aromatics complexes are designed to maximize the yield of benzene and para-xylene. Benzene is a versatile petrochemical building block used in many different products based on its derivation including ethylbenzene, cumene, and cyclohexane. Para-xylene is also an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the HANDBOOK OF PETROLEUM REFINING PROCESSES, 2d. Edition in 1997 by McGraw-Hill.

In an aromatics complex, trace olefins from the catalytic reforming unit must be removed or converted. Untreated olefins would contaminate the highly pure aromatics products as well as contaminate catalysts and adsorbents. Further, olefins remaining in the heavy reformate i.e. reformate splitter bottoms, are typically clay treated to remove the olefins. Olefins must be removed from the heavy reformate so that the xylenes sent to the para-xylene column are low in olefins (Bromine Index<20). With heavier reformates, clay life can be as short as 2-3 months. Alternatively, an Olefin Reduction Process (ORP) unit is generally proposed to replace reformate splitter bottoms clay treater to treat olefins.

Moreover, light olefins in the light reformate stream i.e. reformate splitter overhead, are sent to a aromatics extraction unit where most of the light olefins are rejected to the raffinate stream. The traces that remain in the aromatic extract are clay treated prior to fractionation to obtain benzene and toluene. Therefore, besides treating olefins in heavy reformate i.e. reformate splitter bottoms, aromatics complex operators/owners often need to treat olefins in aromatics extraction raffinate and or LPG stream to meet the olefins specification for downstream unit these respective streams feed into.

Generally, in order to meet the meet the product sec on olefins in the raffinate stream, an ORP unit is installed on full reformate stream. Full reformate contains aromatics i.e. benzene, toluene and xylenes in addition to other light reformate and heavy reformate species. If heavy reformate is fed to ORP unit, it saturates about 5-6 wt % benzene and about 0.5 wt % toluene across the unit. This accounts for significant losses across the ORP unit.

Accordingly, it is desirable to provide an improved method and apparatuses for saturation of olefins present in the reformate stream in an aromatic complex. Further, it is desirable to provide a cost-effective method and apparatus to solve the impending problem of olefins present in aromatics extraction raffinate stream. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to apparatuses and processes for benzene and para-xylene in an aromatics complex. The exemplary embodiments taught herein include apparatuses and processes for producing benzene and para-xylene from a reformate stream in an aromatics complex using a integrated scheme for saturation of olefins present in the reformate stream.

In accordance with another exemplary embodiment, a process is provided for producing benzene and para-xylene from a reformate stream, wherein the process comprises separating the reformate stream to provide a first stream comprising $C_4$ and lighter hydrocarbons and a second stream comprising aromatic hydrocarbons. The second steam is provided to a reformate splitter to provide a reformate bottoms stream comprising $C_{8+}$ aromatic hydrocarbons and a reformate overhead stream comprising $C_{7-}$ aromatic hydrocarbons. The reformate overhead stream is passed to an aromatics extraction unit to provide an aromatics extract stream comprising benzene and toluene and a raffinate stream comprising non-aromatic hydrocarbons. The reformate bottoms stream and one of the first stream and the raffinate stream is passed to an olefin reduction zone, wherein the reformate bottoms stream and one of the first stream and the raffinate stream are contacted with an olefin saturation catalyst under olefin saturation conditions to produce an olefin-treated reformate stream.

In accordance with another exemplary embodiment, a process is provided for process for producing benzene and para-xylene from a reformate stream, wherein the process comprises separating the reformate stream to provide a first stream comprising $C_4$ and lighter hydrocarbons and a second stream comprising aromatic hydrocarbons. The second stream is provided to a reformate splitter to provide a reformate bottoms stream comprising $C_{8+}$ aromatic hydrocarbons and a reformate overhead stream comprising $C_{7-}$ aromatic hydrocarbons. The reformate overhead stream is passed to an aromatics extraction unit to provide an aromatics extract stream comprising benzene and toluene and a raffinate stream comprising non-aromatic hydrocarbons. The aromatics extract stream is passed to a benzene column and subsequently to a toluene column to recover a benzene-enriched stream and a toluene-enriched stream. The reformate bottoms stream and one of the first stream and the raffinate stream is passed to an olefin reduction zone, wherein the reformate bottoms stream and one of the first stream and the raffinate stream are contacted with an olefin saturation catalyst under olefin saturation conditions to produce an olefin-treated reformate stream. The olefin treated reformate stream is passed to an olefin product stripper column to provide an overhead raffinate product stream and a bottoms stripper stream and para-xylene is recovered from the bottoms stripper streams.

In accordance with yet another exemplary embodiment, an apparatus is provided for producing benzene and para-xylene from a catalytic reformate stream, wherein the apparatus comprises a debutanizer to separate the reformate stream to provide a first stream comprising $C_4$ and lighter hydrocarbons in a light ends line and a second stream comprising aromatic hydrocarbons. A reformate splitter is in communication with the debutanizer to provide a reformate bottoms stream in a reformate bottoms line and a reformate overhead stream in a reformate overhead line, from the reformate stream. An aromatics extraction is in communication with the reformate splitter through the reformate overhead line to provide an aromatics extract stream comprising benzene and toluene and a raffinate stream comprising non-aromatic hydrocarbons in a raffinate line. An olefin reduction zone in communication with the reformate bottoms line and in communication with one of the light ends line and the raffinate line to produce an olefin-treated reformate stream in an olefin reduction zone line.

It is an advantage to have a single ORP unit to treat the olefins from at least two of; a reformate splitter bottoms stream, LPG stream from the catalytic reformate unit and the raffinate stream from aromatics extraction unit. The instant integrated scheme for saturation of olefins provides cost benefits in terms of lower CAPEX by employing a single ORP unit. Clay treating unit can still be eliminated resulting in net product yield benefit and no heavies formation. On specification (Olefins content, generally <1 vol % spec) raffinate product can be obtained from extraction unit, which was otherwise worth less and less sellable. Further, On specification LPG is obtained, which was otherwise worth much less. Moreover, the instant flow scheme avoids benzene (about 5 wt %) and toluene (about 0.5 wt %) saturation across the unit. These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following FIGURES, wherein like numerals denote like elements.

Figure 1:
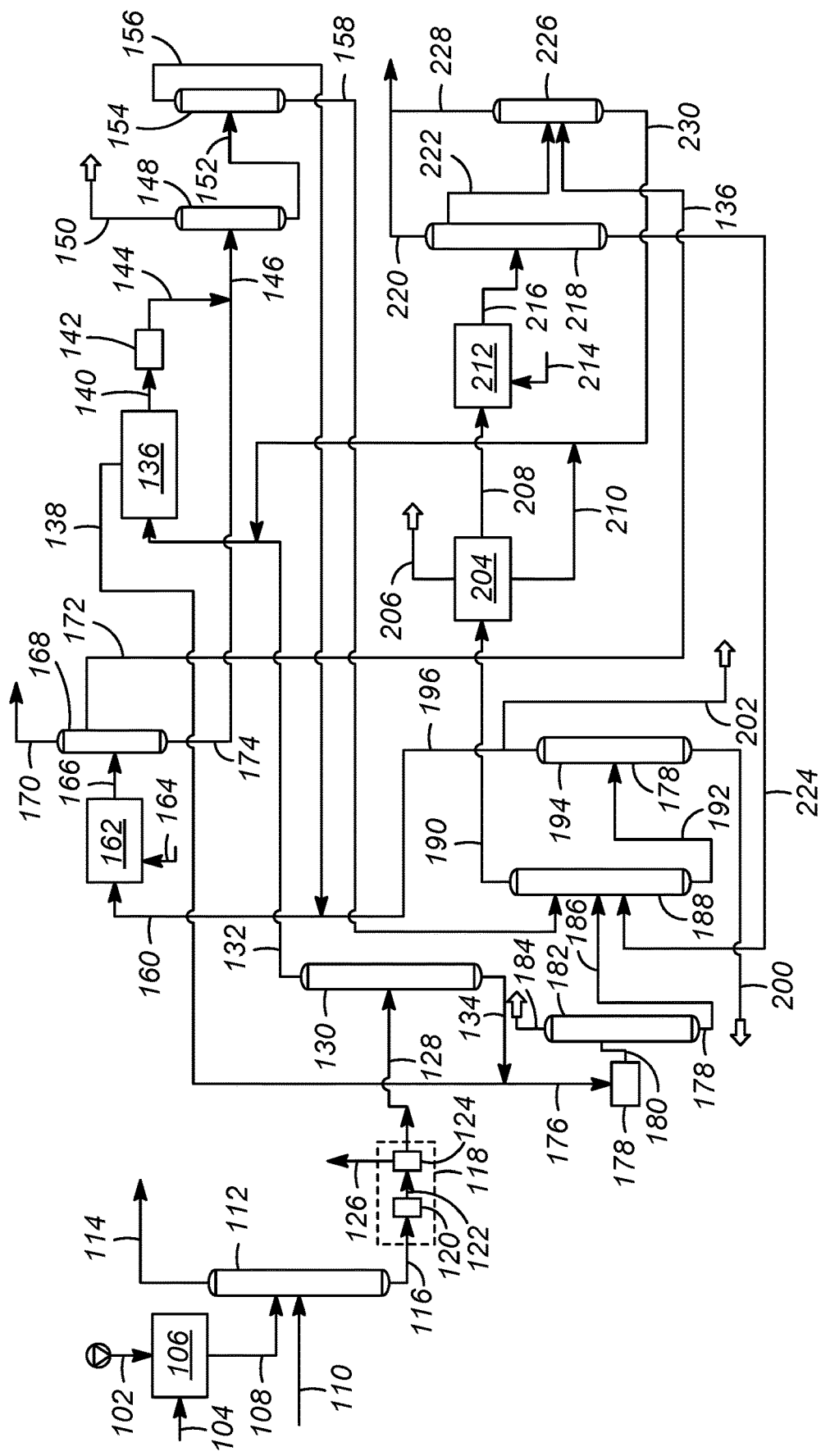
FIG. 1 illustrates an aromatics complex having an integrated olefin saturation scheme according to an embodiment of the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

Definitions

As used herein, the term "stream" can include various hydrocarbon molecules and other substances.

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" or "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally 50%, and preferably 70%, by mole, of a compound or class of compounds in a stream.

As depicted, process flow lines in the FIGURES can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "predominantly" means a majority, suitably at least 50 mol % and preferably at least 60 mol %.

The term "atomic ratio" may be used interchangeably with "mole ratio".

The term "feeding" means that the feed passes from a conduit or vessel directly to an object without passing through an intermediate vessel.

The term "passing" includes "feeding" and means that the material passes from a conduit or vessel to an object.

As used herein, the term "kilopascal" may be abbreviated "kPa" and the term "megapascal" may be abbreviated "MPa", and all pressures disclosed herein are absolute.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. Moreover, the reaction conditions including selection of temperature, pressure, LHSV and catalyst in the various units in the aromatics complex described below are conventional which are known to one of ordinary skill in the art, unless wherever mentioned.

An embodiment of a process and apparatus for producing benzene and para-xylene in an aromatics complex is addressed with reference to a process and apparatus 100 illustrating an aromatics complex having an integrated olefin saturation scheme according to an embodiment as shown in FIG. 1. The process and apparatus 100 includes a hydrotreating zone 106, a naphtha splitter 112, a reforming zone 118 including a catalytic reforming unit 120 and a debutanizer 124, a reformate splitter 130, an aromatics extraction unit 136, a clay treater 142, a benzene column 148, a toluene column 154, a transalkylation zone 162, a transalkylation stripper 168, an olefin reduction zone 178, an olefin product stripper column 182, a xylene fractionation column 188, a heavy aromatics column 194, a para-xylene column 204, an isomerization column 212, an isomerization deheptanizer column 218 and an isomerization stripper column 226.

In accordance with an exemplary embodiment as shown in FIG. 1, a hydrocarbon feedstream in line 102 may be passed to the hydrotreating zone 106. In accordance with the instant embodiment as discussed, the hydrocarbon feedstream in line 102 is a naphtha stream and hence interchangeably referred to as naphtha stream in line 102. The naphtha stream in line 102 may be provided to the hydrotreating zone 106 to produce a hydrotreated naphtha stream in line 108. As used herein, the term "naphtha" means the hydrocarbon material boiling in the range between about 10° C. and about 200° C. atmospheric equivalent boiling point (AEBP) as determined by any standard gas chromatographic simulated distillation method such as ASTM D2887, all of which are used by the petroleum industry. The hydrocarbon material may be more contaminated and contain a greater amount of aromatic compounds than is typically found in refinery products. The typical petroleum derived naphtha contains a wide variety of different hydrocarbon types including normal paraffins, branched paraffins, olefins, naphthenes, benzene, and alkyl aromatics. Although the present embodiment is exemplified by a naphtha feedstream, the process is not limited to a naphtha feedstream, and can include any feedstream with a composition that overlaps with a naphtha feedstream.

Referring to FIG. 1, a make-up gas stream in line 104 may also be provided to the hydrotreating zone 106. The make-up gas stream in line 104 may predominantly comprise hydrogen. The hydrotreating zone 106 may include one or more hydrotreating reactors for removing sulfur and nitrogen from the naphtha stream in line 102. A number of reactions take place in the hydrotreating zone 106 including hydrogenation of olefins and hydrodesulfurization of mercaptans and other organic sulfur compounds; both of which (olefins, and sulfur compounds) are present in the naphtha fractions. Examples of sulfur compounds that may be present include dimethyl sulfide, thiophenes, benzothiophenes, and the like. Further, reactions in the hydrotreating zone 106 include removal of heteroatoms, such as nitrogen and metals. Conventional hydrotreating reaction conditions are employed in the hydrotreating zone 106 which are known to one of ordinary skill in the art.

The hydrotreated naphtha stream in line 108 withdrawn from the hydrotreating zone 106 may be passed to the naphtha splitter 112. Further, a hydrocracked heavy naphtha stream in line 110 may also be passed to the naphtha splitter 112. A light naphtha stream in line 114 comprising $C_5$ and $C_6$ hydrocarbons and a heavy naphtha stream in line 116 are withdrawn from the naphtha splitter 112. In accordance with an exemplary embodiment as shown in the FIG. 1, the heavy naphtha stream in line 116 may be passed to the catalytic reforming unit 120 in the reforming zone 118 to provide a reformate stream in line 122. In an aspect, the hydrotreated naphtha stream in line 108 may be passed to the catalytic reforming unit 120 to provide the reformate stream in line 122. The reforming conditions includes a temperature of from about 300° C. to about 500° C., and a pressure from about 0 kPa(g) to about 3500 kPa(g). Reforming catalysts generally comprise a metal on a support. This catalyst is conventionally a dual-function catalyst that includes a metal hydrogenation-dehydrogenation catalyst on a refractory support. The support can include a porous material, such as an inorganic oxide or a molecular sieve, and a binder with a weight ratio from 1:99 to 99:1. In accordance with various embodiments, the reforming catalyst comprises a noble metal comprising one or more of platinum, palladium, rhodium, ruthenium, osmium, and iridium. The reforming catalyst may be supported on refractory inorganic oxide support comprising one or more of alumina, a chlorided alumina a magnesia, a titania, a zirconia, a chromia, a zinc oxide, a thoria, a boria, a silica-alumina, a silica-magnesia, a chromia-alumina, an alumina-boria, a silica-zirconia and a zeolite.

The reformate stream in line 122 may be passed to the debutanizer 124. In the debutanizer 124, the reformate stream in line 122 may be separated to provide a first stream in line 126 comprising $C_4$ and lighter hydrocarbons and a second stream in line 128 comprising aromatic hydrocarbons. In an aspect, the reforming zone 118 may further comprise one or more separators for separation of a hydrogen-rich stream and a stream comprising $C_5$ hydrocarbons to obtain the second stream in line 128 which is subsequently processed further as described below.

The second steam in line 128 may be passed to the reformate splitter 130 to provide a reformate overhead stream in line 132 comprising $C_{7-}$ aromatic hydrocarbons and a reformate bottoms stream in line 134 comprising $C_{8+}$ aromatic hydrocarbons. The reformate overhead stream in line 132 may be passed to the aromatics extraction unit 136 In accordance with an exemplary embodiment as shown in the FIG. 1, a stripper bottoms stream in line 230 from the isomerization stripper column 226 may also be passed to the aromatics extraction unit 136. The aromatics extraction unit 136 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art. An aromatics extract stream in line 140 comprising benzene and toluene and a raffinate stream in line 138 comprising non-aromatic hydrocarbons may be withdrawn from the aromatics extraction unit 136.

Referring back to the reformate splitter 130, the reformate bottoms stream in line 134 may be passed to the olefin reduction zone 178. The raffinate stream in line 138 may also be passed to the olefin reduction zone 178. In accordance with an exemplary embodiment as shown in FIG. 1, the reformate bottoms stream in line 134 and the raffinate stream in line 138 mix to form a combined stream in line 176 which may be subsequently passed to the olefin reduction zone 178. The raffinate stream in line 138 may be in downstream communication with the reformate bottoms line 134. Accordingly, the olefin reduction zone 178 may be in downstream communication with the reformate bottoms line 134 and in downstream communication with the raffinate line 138. In an aspect, the reformate bottoms stream in line 134 and the raffinate stream in line 138 may be passed directly to the olefin reduction zone 178. Accordingly, the olefin reduction zone 178 may be in direct communication with the reformate bottoms line 134 and in direct communication with the raffinate line 138.

In the olefin reduction zone 178, the reformate bottoms stream in line 134 and the raffinate stream in line 178 are contacted with an olefin saturation catalyst under olefin saturation conditions to produce an olefin-treated reformate stream in olefin reduction zone line 180. In the olefin reduction zone 178, the olefins present in the reformate bottoms stream in line 134 and the raffinate stream in line 138 are converted to useful products. Thus, the catalytic olefin saturation helps improve the economics of the flow scheme. Suitable olefin saturation catalysts in the present disclosure contain elemental nickel or a platinum-group component preferably supported on an inorganic oxide support, which is typically alumina. In the case where the elemental nickel is present on a support, the nickel is preferably present in an amount from about 2 to about 40 wt % of the total catalyst weight. Typical olefin saturation conditions include a temperature from about 20° C. to about 200° C., a pressure from about 5 kg/cm$^2$ to about 70 kg/cm$^2$ and a stoichiometric ratio of hydrogen to olefins from about 1:1 to about 5:1.

Subsequently, the olefin-treated reformate stream in olefin reduction zone line 180 may be passed to the olefin product stripper column 182 to provide an overhead raffinate product stream in an olefin product stripper overhead in line 184 and a bottoms stripper stream in line 186.

Referring back to aromatics extraction unit 136, the aromatics extract stream in line 140 comprising benzene and toluene may be passed to a benzene column 148 and subsequently to a toluene column 154 to recover a benzene-enriched stream in line 150 and a toluene-enriched stream in line 156. In accordance with an exemplary embodiment as shown in FIG. 1, the aromatics extract stream in line 140 may be passed to the clay treater 142. In the clay treater 142, the aromatics extract in line 140 may be treated to remove trace olefins to provide an aromatics effluent stream in line 144 which may be subsequently passed to the benzene column 148. The clay treater 142 may consist of the well-known clay treating means or other means to treat residual olefin contaminants. In accordance with an exemplary embodiment as shown in FIG. 1, the aromatics effluent stream in line 144 may combine with a transalkylation stripper bottoms stream in line 174 to provide a mixed stream in line 146 which may be subsequently fed to the benzene column 148. The benzene-enriched stream in line 150 and benzene column bottoms stream in line 152 comprising $C_7$ and heavier hydrocarbons are withdrawn from the benzene column 148. The benzene column bottoms stream in line 152 may be passed to the toluene column 154. The toluene-enriched stream in line 156 may be produced from the overhead of the toluene column 154 and sent to the transalkylation zone 162, with the bottom of the toluene column 154 producing the toluene column bottoms stream in line 158 rich in xylenes. The toluene column bottoms stream in line 158 from the bottom of the toluene column 154 may be sent to a xylene fractionation column 188 as described later in the specification. In accordance with an exemplary embodiment as shown in FIG. 1, the toluene-enriched stream in line 156 may be blended with a heavy aromatics column overhead stream in line 196 rich in $C_9$ and $C_{10}$ alkylaromatics to provide a transalkylation feed stream in line 160 which may be subsequently fed to the transalkylation zone 162 for production of additional xylenes and benzene. A make-up hydrogen gas stream in line 164 may also be provided to the transalkylation zone 162. In the transalkylation zone 162, transalkylation feed stream in line 160 may be contacted with a transalkylation catalyst under transalkylation conditions. In the transalkylation zone 162, the process continues by transalkylating $C_9$ and $C_{10}$ alkylaromatics present in the heavy aromatics column overhead stream in line 196 with the toluene-enriched stream in line 156. A transalkylated stream in line 166 comprising benzene and xylenes may be withdrawn from the transalkylation zone 162.

Transalkylation catalysts that can be used in the present disclosure include conventional transkylation catalysts such as those disclosed in U.S. Pat. No. 6,740,788, the teachings of which are incorporated herein by reference. Conditions employed in the transalkylation zone 162 normally include a temperature of from about 200° C. to about 540° C. The transalkylation zone 162 is operated at moderately elevated pressures broadly ranging from about 1 kg/cm$^2$. to about 60 kg/cm$^2$. The transalkylation reaction can be effected over a wide range of space velocities, with higher space velocities effecting a higher ratio of para-xylene at the expense of conversion. Liquid hourly space velocity generally is in the range of from about 0.1 to about 20 hr$^{-1}$.

The transalkylated stream in line 166 may be sent to transalkylation stripper 168 to recover the transalkylation stripper bottoms stream in line 174 comprising benzene and xylenes. Light ends comprising $C_{6-}$ hydrocarbons may be removed in transalkylation stripper overhead stream in line 170. A net overhead stream in line 172 comprising $C_5$ to $C_7$ hydrocarbons may also be withdrawn from the transalkylation stripper 168. Subsequently, the transalkylation stripper bottoms stream in line 174 may be combined with the aromatics effluent stream in line 144 to provide the mixed stream in line 146 which may be subsequently fed to the benzene column 148 and further downstream processing as previously described.

Referring back to the olefin product stripper column 182, the bottoms stripper stream in line 186 from the olefin product stripper column 182 may be passed to the xylene fractionation column 188. In accordance with an exemplary embodiment as shown in FIG. 1, the toluene column bottoms stream in line 158 rich in xylenes may also be sent to the xylene fractionation column 188. Further, a bottoms stream in line 224 from isomerization deheptanizer column 218 may also be passed to the xylene fractionation column 188. An overhead xylene stream in line 190 comprising mixed xylenes and a xylene fractionator bottoms stream in line 192 rich in $C_9$ and heavier alkylaromatic hydrocarbons are produced in the xylene fractionation column 188.

The xylene fractionator bottoms stream in line 192 may be passed to the heavy aromatics column 194 to separate heavy aromatics comprising $C_{11+}$ alkylaromatic hydrocarbons from $C_9$ and $C_{10}$ alkylaromatics recovered as the heavy aromatics column overhead stream in line 196. The $C_{11+}$ alkylaromatic hydrocarbons may be withdrawn from the heavy aromatics column 194 as a bottoms stream in line 200. The heavy aromatics column overhead stream in line 196 rich in $C_9$ and $C_{10}$ alkylaromatics may be blended with the toluene-enriched stream in line 156 to provide the transalkylation feed stream in line 160 which may be subsequently provide to the transalkylation zone 162 for production of additional xylenes and benzene as previously described. In accordance with an exemplary embodiment as shown in FIG. 1, a portion of the heavy aromatics column overhead stream in line 196 comprising $C_9$ and $C_{10}$ alkylaromatics may be withdrawn as a second intermediate stream in line 202 and may be sent as a product to gasoline blending.

Referring back to the xylene fractionation column 188, the overhead xylene stream in line 190 may be passed to the para-xylene column 204 to recover a para-xylene product stream in line 206, mixed xylenes stream in line 208 and a xylene raffinate stream in line 210 comprising toluene. The para-xylene column 204 may be based on a fractional crystallization process or an adsorptive separation process, both of which are well known in the art, and preferably is based on the adsorptive separation process. Such adsorptive separation can recover over 99 wt % pure para-xylene at high recovery per pass. The mixed xylenes stream in line 208 and a make-up hydrogen gas stream in line 214 may be passed to the isomerization column 212 wherein the mixed xylenes stream in line 208 may be contacted with an isomerization catalyst under isomerization conditions to produce an isomerization product stream in line 216 to subsequently recover additional para-xylene. Additional para-xylene is produced by reestablishing an equilibrium or near-equilibrium distribution of xylene isomers. Any ethylbenzene in the para-xylene separation unit raffinate is either converted to additional xylenes or converted to benzene by dealkylation, depending upon the type of isomerization catalyst used. Isomerization catalyst that can be used in the present disclosure include conventional transkylation catalysts such as those disclosed in U.S. Pat. No. 6,740,788, the teachings of which are incorporated herein by reference.

Typical isomerization conditions include a temperature in the range from about 0° C. to about 600° C. and a pressure from atmospheric to about 50 kg/cm². The liquid hourly hydrocarbon space velocity of the feedstock relative to the volume of catalyst is from about 0.1 to about 30 hr$^{-1}$. The hydrocarbon contacts the catalyst in admixture with the make-up hydrogen gas stream in line 214 at a hydrogen-to-hydrocarbon mole ratio of from about 0.5:1 to 15:1 or more, and preferably a ratio of from about 0.5 to 10. The xylene raffinate stream in line 210 comprising toluenes may be mixed with the stripper bottoms stream in line 230 from the isomerization stripper column 226 and passed to the aromatics extraction unit 136 as previously described.

The isomerization product stream in line 216 from the isomerization column 212 may be sent to the isomerization deheptanizer column 218. The bottom stream in line 224 obtained from the isomerization deheptanizer column comprises $C_{7+}$ aromatics (primarily mixed xylenes) and may be recycled back to the xylenes fractionation column 188 as previously described. An overhead stream in line 220 comprising light ends including $C_{6-}$ hydrocarbons and a liquid stream in line 222 comprising liquid products are also obtained from the isomerization deheptanizer column 218. The liquid stream in line 222 and the net overhead stream in line 172 from the transalkylation stripper 168 may be passed to the isomerization stripper column 226 to obtain a stripper overhead stream in line 228 comprising light ends and the stripper bottoms stream in line 230 comprising $C_6$ and $C_7$ hydrocarbons. The stripper overhead stream in line 228 may combine with the overhead stream in line 220 and rejected as light ends. Further, the stripper bottom stream in line 230 may be recycled to aromatics extraction unit 136 as previously described.

Figure 2:
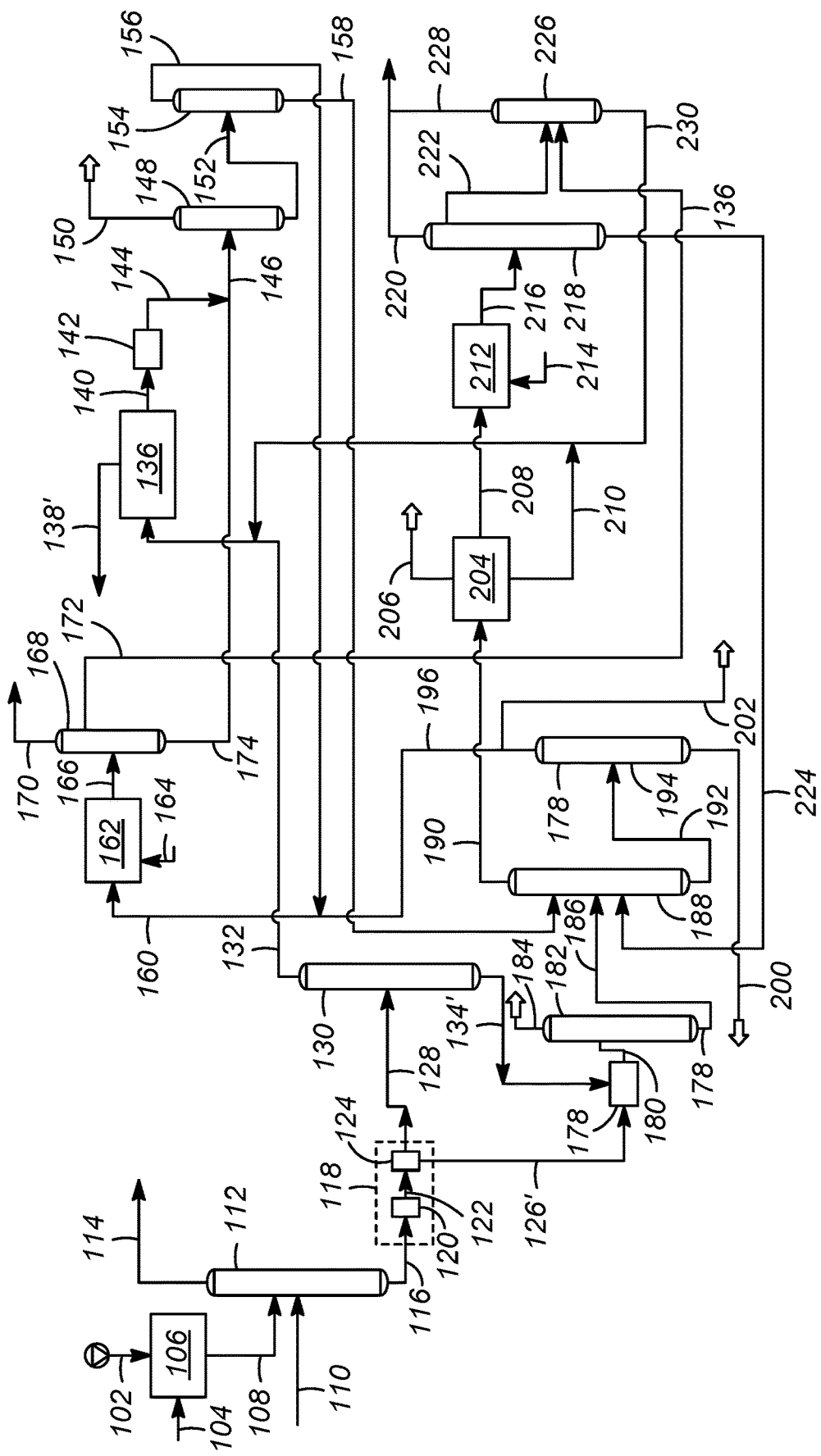
FIG. 2 illustrates an aromatics complex having an integrated olefin saturation scheme according to another embodiment another embodiment of the present disclosure.

Turning now to FIG. 2, another embodiment of the aromatics complex is addressed with reference to a process and apparatus 200 providing an alternative integrated olefin saturation scheme. Many of the elements in FIG. 2 have the same configuration as in FIG. 1 and bear the same respective reference number and have similar operating conditions. Elements in FIG. 2 that correspond to elements in FIG. 1 but have a different configuration bear the same reference numeral as in FIG. 1 but are marked with a prime symbol ('). Further, the temperature, pressure and composition of various streams are similar to the corresponding streams in FIG. 1, unless specified otherwise. The apparatus and process in FIG. 2 are the same as in FIG. 1 with the exception of the noted following differences. In accordance with the exemplary embodiment as shown in the FIG. 2, the reformate stream in line 122 obtained from the catalytic reforming unit 120 may passed to the debutanizer 124 to obtain a first stream in line 126' comprising $C_4$ and lighter hydrocarbons and the second stream in line 128 comprising aromatic hydrocarbons. The second steam in line 128 may be passed to the reformate splitter 130 to provide the reformate overhead stream in line 132 comprising $C_{7-}$ aromatic hydrocarbons and a reformate bottoms stream in line 134' comprising $C_{8+}$ aromatic hydrocarbons. The reformate overhead stream in line 132 may be passed to the aromatics extraction unit 136 to provide the aromatics extract stream in line 140 comprising benzene and toluene and a raffinate stream in line 138' comprising non-aromatic hydrocarbons. The aromatics extract stream in line 140 processed further as described with respect to FIG. 1.

The first stream in line 126' and the reformate bottoms stream in line 134' may be passed to the olefin reduction zone 178. Accordingly, the olefin reduction zone 178 may be in downstream communication with the first stream in line 126' and the reformate bottoms stream in line 134'. In accordance with an exemplary embodiment as shown in FIG. 2, both the first stream in line 126' and the reformate bottoms stream in line 134' are fed directly to the olefin reduction zone 178. Accordingly, the olefin reduction zone 178 may be in direct communication with the first stream in line 126' and the reformate bottoms stream in line 134'. In an aspect, the first stream in line 126' and the reformate bottoms stream in line 134' may be combined prior to being fed to the olefin reduction zone 178. In another aspect, the first stream in line 126', the reformate bottoms stream in line 134' and the raffinate stream in line 138' may be fed to the olefin reduction zone 178. In such as aspect, the olefin reduction zone 178 may be in downstream communication with the first stream in line 126', the reformate bottoms stream in line 134' and the raffinate stream in line 138'. The olefin-treated reformate stream in olefin reduction zone line 180 may be obtained from the olefin reduction zone 178 which is processed further as described with respect to FIG. 1.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing benzene and para-xylene from a reformate stream, wherein the process comprises a) separating the reformate stream to provide a first stream comprising $C_4$ and lighter hydrocarbons and a second stream comprising aromatic hydrocarbons; b) providing the second steam to a reformate splitter to provide a reformate bottoms stream comprising $C_{8+}$ aromatic hydrocarbons and a reformate overhead stream comprising $C_{7-}$ aromatic hydrocarbons; c)

passing the reformate overhead stream to an aromatics extraction unit to provide an aromatics extract stream comprising benzene and toluene and a raffinate stream comprising non-aromatic hydrocarbons; and d) passing the reformate bottoms stream and one of the first stream and the raffinate stream to an olefin reduction zone, wherein the reformate bottoms stream and one of the first stream and the raffinate stream are contacted with an olefin saturation catalyst under olefin saturation conditions to produce an olefin-treated reformate stream. An embodiment of the invention is one, any or all of prior embodiments in this paragraph up through the first embodiment in this paragraph further comprising providing a naphtha stream to a hydrotreating zone to produce a hydrotreated naphtha stream and passing the hydrotreated naphtha stream to a catalytic reforming unit, wherein the hydrotreated naphtha stream is contacted with a reforming catalyst under reforming conditions to produce the reformate stream comprising aromatic hydrocarbons and light-end hydrocarbons. An embodiment of the invention is one, any or all of prior embodiments in this paragraph up through the first embodiment in this paragraph further comprising passing the hydrotreated naphtha stream and a hydrocracked heavy naphtha stream to a naphtha splitter to provide a light naphtha stream and a heavy naphtha stream, wherein passing the hydrotreated naphtha stream comprises passing the heavy naphtha stream to the catalytic reforming unit. An embodiment of the invention is one, any or all of prior embodiments in this paragraph up through the first embodiment in this paragraph further comprising passing the olefin-treated reformate stream to an olefin product stripper column to provide an overhead raffinate product stream and a bottoms stripper stream. An embodiment of the invention is one, any or all of prior embodiments in this paragraph up through the first embodiment in this paragraph further comprising passing the bottoms stripper stream to a xylene fractionation column to produce an overhead xylene stream and a xylene fractionator bottoms stream rich in $C_9$ and heavier alkylaromatic hydrocarbons. An embodiment of the invention is one, any or all of prior embodiments in this paragraph up through the first embodiment in this paragraph further comprising passing the overhead xylene stream to a para-xylene column to recover a para-xylene product stream, mixed xylenes stream and a xylene raffinate stream. An embodiment of the invention is one, any or all of prior embodiments in this paragraph up through the first embodiment in this paragraph further comprising passing the mixed xylenes stream and a hydrogen stream to an isomerization column wherein the mixed xylenes stream is contacted with an isomerization catalyst under isomerization conditions to produce an isomerization product stream and subsequently recover para-xylene from the isomerization product. An embodiment of the invention is one, any or all of prior embodiments in this paragraph up through the first embodiment in this paragraph further comprising passing the xylene fractionator bottoms stream to a heavy aromatics column to separate heavy aromatics from $C_9$ and $C_{10}$ alkylaromatics recovered as a heavy aromatics column overhead stream. An embodiment of the invention is one, any or all of prior embodiments in this paragraph up through the first embodiment in this paragraph further comprising passing the aromatics extract stream comprising benzene and toluene to a benzene column and subsequently to a toluene column to recover a benzene-enriched stream and a toluene-enriched stream. An embodiment of the invention is one, any or all of prior embodiments in this paragraph up through the first embodiment in this paragraph further comprising passing the heavy aromatics column overhead stream and the toluene-enriched stream to an transalkylation column to provide a transalkylated stream comprising benzene and xylene. An embodiment of the invention is one, any or all of prior embodiments in this paragraph up through the first embodiment in this paragraph further comprising passing the transalkylated stream to a transalkylation stripper to recover a transalkylation stripper bottoms stream comprising benzene and toluene and passing the transalkylation stripper bottoms stream to the benzene column and subsequently to the toluene column. An embodiment of the invention is one, any or all of prior embodiments in this paragraph up through the first embodiment in this paragraph further comprising passing a toluene column bottoms stream from the toluene column to the xylene fractionation column.

A second embodiment of the invention is a process for producing benzene and para-xylene from a reformate stream, wherein the process comprises a) separating the reformate stream to provide a first stream comprising $C_4$ and lighter hydrocarbons and a second stream comprising aromatic hydrocarbons; b) providing the second stream to a reformate splitter to provide a reformate bottoms stream comprising $C_{8+}$ aromatic hydrocarbons and a reformate overhead stream comprising $C_{7-}$ aromatic hydrocarbons; c) passing the reformate overhead stream to an aromatics extraction unit to provide an aromatics extract stream comprising benzene and toluene and a raffinate stream comprising non-aromatic hydrocarbons; d) passing the aromatics extract stream to a benzene column and subsequently to a toluene column to recover a benzene-enriched stream and a toluene-enriched stream; e) passing the reformate bottoms stream and one of the first stream and the raffinate stream to an olefin reduction zone, wherein the reformate bottoms stream and one of the first stream and the raffinate stream are contacted with an olefin saturation catalyst under olefin saturation conditions to produce an olefin-treated reformate stream; f) passing the olefin treated reformate stream to an olefin product stripper column to a provide an overhead raffinate product stream and a bottoms stripper stream; and g) recovering para-xylene from the bottoms stripper streams. An embodiment of the invention is one, any or all of prior embodiments in this paragraph up through the second embodiment in this paragraph further comprising providing a naphtha stream to a hydrotreating zone to produce a hydrotreated naphtha stream and passing the hydrotreated naphtha stream to a catalytic reforming unit, wherein the hydrotreated naphtha stream is contacted with a reforming catalyst under reforming conditions to produce the reformate stream comprising aromatic components and light-end hydrocarbons. An embodiment of the invention is one, any or all of prior embodiments in this paragraph up through the second embodiment in this paragraph, wherein the recovery of para-xylene comprises passing the bottoms stripper stream to a xylene fractionation column to produce an overhead xylene stream and a xylene fractionator bottoms stream rich in $C_9$ and heavier alkylaromatic hydrocarbons and passing the overhead xylene stream to a para-xylene column to recover a para-xylene product stream. An embodiment of the invention is one, any or all of prior embodiments in this paragraph up through the second embodiment in this paragraph further comprising passing the xylene fractionator bottoms stream to a heavy aromatics column to separate heavy aromatics from $C_9$ and $C_{10}$ alkylaromatics recovered as a heavy aromatics column overhead stream. An embodiment of the invention is one, any or all of prior embodiments in this paragraph up through the second embodiment in this paragraph further comprising passing the heavy aromatics column overhead stream and the toluene-enriched stream to an transalkylation column to provide a transalkylated stream comprising benzene and xylene. An embodiment of the invention is one, any or all of prior embodiments in this paragraph up through the second embodiment in this paragraph further comprising passing a toluene column bottoms stream from the toluene column to the xylene fractionation column.

A third embodiment of the invention is an apparatus for producing benzene and para-xylene from a catalytic reformate stream, wherein the apparatus comprises a) a debutanizer to separate the reformate stream to provide a first stream comprising $C_4$ and lighter hydrocarbons in a light ends line and a second stream comprising aromatic hydrocarbons, b) a reformate splitter in communication with the debutanizer to provide a reformate bottoms stream in a reformate bottoms line and a reformate overhead stream in a reformate overhead line, from the reformate stream; c) an aromatics extraction in communication with the reformate splitter through the reformate overhead line to provide an aromatics extract stream comprising benzene and toluene and a raffinate stream comprising non-aromatic hydrocarbons in a raffinate line; and d) an olefin reduction zone in communication with the reformate bottoms line and in communication with one of the light ends line and the raffinate line to produce an olefin-treated reformate stream in an olefin reduction zone line. An embodiment of the invention is one, any or all of prior embodiments in this paragraph up through the third embodiment in this paragraph further comprising an olefin product stripper column in communication with olefin reduction zone through the olefin reduction zone line to provide an overhead raffinate product stream in an olefin product stripper overhead line and a bottoms stripper stream in a bottoms stripper line.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by volume (mole), unless otherwise indicated.

The invention claimed is:

1. A process for producing benzene and para-xylene from a reformate stream, wherein the process comprises:
    a) separating the reformate stream to provide a first stream comprising $C_4$ and lighter hydrocarbons and a second stream comprising aromatic hydrocarbons;
    b) providing the second stream to a reformate splitter to provide a reformate bottoms stream comprising $C_{8+}$ aromatic hydrocarbons and a reformate overhead stream comprising $C_{7-}$ aromatic hydrocarbons;
    c) passing the reformate overhead stream to an aromatics extraction unit to provide an aromatics extract stream comprising benzene and toluene and a raffinate stream comprising non-aromatic hydrocarbons;
    d) passing the reformate bottoms stream and one of the first stream and the raffinate stream to an olefin reduction zone, wherein the reformate bottoms stream and one of the first stream and the raffinate stream are contacted with an olefin saturation catalyst under olefin saturation conditions to produce an olefin-treated reformate stream; and
    e) recovering a para-xylene product stream from the olefin-treated reformate stream.

2. The process of claim 1 further comprising providing a naphtha stream to a hydrotreating zone to produce a hydrotreated naphtha stream and passing at least a portion of the hydrotreated naphtha stream to a catalytic reforming unit, wherein said at least the portion of the hydrotreated naphtha stream is contacted with a reforming catalyst under reforming conditions to produce the reformate stream comprising aromatic hydrocarbons and $C_4$ and lighter hydrocarbons.

3. The process of claim 2 further comprising passing the hydrotreated naphtha stream and a hydrocracked heavy naphtha stream to a naphtha splitter to provide a light naphtha stream and a heavy naphtha stream before passing said at least the portion of the hydrotreated naphtha stream to the catalytic reforming unit, and wherein passing said at least the portion of the hydrotreated naphtha stream to the catalytic reforming unit comprises passing the heavy naphtha stream to the catalytic reforming unit.

4. The process of claim 1 wherein recovering the para-xylene product stream from the olefin-treated reformate stream comprises passing the olefin-treated reformate stream to an olefin product stripper column to provide an overhead raffinate product stream and a bottoms stripper stream and recovering the para-xylene product stream from the bottoms stripper stream.

5. The process of claim 4 wherein recovering the para-xylene product stream from the bottoms stripper stream comprises passing the bottoms stripper stream to a xylene fractionation column to produce an overhead xylene stream and a xylene fractionator bottoms stream rich in $C_9$ and heavier alkylaromatic hydrocarbons and recovering the para-xylene product stream from the overhead xylene stream.

6. The process of claim 1 wherein recovering the para-xylene product stream from the overhead xylene stream comprises passing the overhead xylene stream to a para-xylene column to recover the para-xylene product stream, a mixed xylenes stream, and a xylene raffinate stream.

7. The process of claim 6 further comprising contacting the mixed xylenes stream with an isomerization catalyst in the presence of hydrogen in an isomerization column under isomerization conditions to produce an isomerization product stream and subsequently recovering para-xylene from the isomerization product stream.

8. The process of claim 5 further comprising passing the xylene fractionator bottoms stream to a heavy aromatics column to separate heavy aromatics from $C_9$ and $C_{10}$ alkylaromatics recovered as a heavy aromatics column overhead stream.

9. The process of claim 8 further comprising passing the aromatics extract stream comprising benzene and toluene to a benzene column forming a benzene-enriched stream and a benzene column bottoms stream, and passing the benzene column bottoms stream to a toluene column forming a toluene-enriched stream and a toluene column bottoms stream, and recovering the benzene-enriched stream and the toluene-enriched stream.

10. The process of claim 9 further comprising passing the heavy aromatics column overhead stream and the toluene-enriched stream to an transalkylation zone to provide a transalkylated stream comprising benzene and xylene.

11. The process of claim 10 further comprising passing the transalkylated stream to a transalkylation stripper to recover a transalkylation stripper bottoms stream comprising benzene and toluene and passing the transalkylation stripper bottoms stream to the benzene column and subsequently to the toluene column.

12. The process of claim 11 further comprising passing a toluene column bottoms stream from the toluene column to the xylene fractionation column.

13. A process for producing benzene and para-xylene from a reformate stream, wherein the process comprises:
   a) separating the reformate stream to provide a first stream comprising $C_4$ and lighter hydrocarbons and a second stream comprising aromatic hydrocarbons;
   b) providing the second stream to a reformate splitter to provide a reformate bottoms stream comprising $C_{8+}$ aromatic hydrocarbons and a reformate overhead stream comprising $C_{7-}$ aromatic hydrocarbons;
   c) passing the reformate overhead stream to an aromatics extraction unit to provide an aromatics extract stream comprising benzene and toluene and a raffinate stream comprising non-aromatic hydrocarbons;
   d) passing the aromatics extract stream to a benzene column to forming a benzene-enriched stream and a benzene column bottoms stream, and passing the benzene column bottoms stream to a toluene column forming a toluene-enriched stream and a toluene column bottoms stream, and recovering the benzene-enriched stream and the toluene-enriched stream;
   e) passing the reformate bottoms stream and one of the first stream and the raffinate stream to an olefin reduction zone, wherein the reformate bottoms stream and one of the first stream and the raffinate stream are contacted with an olefin saturation catalyst under olefin saturation conditions to produce an olefin-treated reformate stream;
   f) passing the olefin treated reformate stream to an olefin product stripper column to a provide an overhead raffinate product stream and a bottoms stripper stream; and
   g) recovering para-xylene from the bottoms stripper streams.

14. The process of claim 13 further comprising providing a naphtha stream to a hydrotreating zone to produce a hydrotreated naphtha stream and passing the hydrotreated naphtha stream to a catalytic reforming unit, wherein said hydrotreated naphtha stream is contacted with a reforming catalyst under reforming conditions to produce the reformate stream comprising aromatic components and $C_4$ and lighter hydrocarbons.

15. The process of claim 13, wherein the recovery of para-xylene comprises passing the bottoms stripper stream to a xylene fractionation column to produce an overhead xylene stream and a xylene fractionator bottoms stream rich in $C_9$ and heavier alkylaromatic hydrocarbons and passing the overhead xylene stream to a para-xylene column to recover a para-xylene product stream.

16. The process of claim 15 further comprising passing the xylene fractionator bottoms stream to a heavy aromatics column to separate heavy aromatics from $C_9$ and $C_{10}$ alkylaromatics recovered as a heavy aromatics column overhead stream.

17. The process of claim 16 further comprising passing the heavy aromatics column overhead stream and the toluene-enriched stream to an transalkylation zone to provide a transalkylated stream comprising benzene and xylene.

18. The process of claim 13 further comprising passing a toluene column bottoms stream from the toluene column to the xylene fractionation column.

* * * * *